United States Patent [19]

Shoesmith et al.

[11] Patent Number: Plant 6,778

[45] Date of Patent: May 2, 1989

[54] CHRYSANTHEMUM PLANT NAMED JAZZ

[75] Inventors: Leonard H. Shoesmith, late of Westfield, England, by May Victoria Shoesmith, Executrix; Peter S. Hesse, Bradenton, Fla.

[73] Assignee: Ball Seed Company, West Chicago, Ill.

[21] Appl. No.: 140,128

[22] Filed: Dec. 31, 1987

[51] Int. Cl.[4] ..... A01H 5/00

[52] U.S. Cl. ..... Plt./74

[58] Field of Search ..... Plt./74

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A Chrysanthemum plant named Jazz having anemone flower form, white ray floret color, bright yellow disc florets, seven week flowering response; compact, cushion growth habit, and freely branching and profuse flowering habits.

1 Drawing Sheet

The present invention comprises a new and distinct cultivar of *Chrysanthemum morifolium,* hereinafter referred to by the cultivar name Jazz.

Jazz is a product of a planned breeding program which had the objective of creating new Chrysanthemum cultivars with compact growth habit, white ray florets, early flowering, and anemone type flowers making it suitable for production as a garden mum. Such traits in combination were not present or needed improvement in previously available commercial cultivars.

Jazz was originated from a hybridization made in a controlled breeding program is Westfiled Woking, England by Leonard Shoesmith in 1980. both the female and male parents are unknown at this time.

Jazz was discovered and selected as one flowering plant within the progeny of the stated parentage by Peter S. Hesse in November 1981 in a controlled environment in Parrish, Fla.

The first act of asexual reproduction of Jazz was accomplished when vegetative cuttings were taken from the initial selection in March 1982 in a controlled environment in Parrish, Fla. by a technician working under formulations established and supervised by Peter S. Hesse. Horticultural examination of selected units initiated in September 1982 has demonstrated that the combination of characteristics as herein disclosed for Jazz are firmly fixed and are retained through successive generations of asexual reproduction.

The following traits have been repeatedly observed and are determined to be basic characteristic of Jazz, which in combination distinguish this Chrysanthemum as a new and distinct cultivar:

1. Seven week flower response.
2. White ray florets, and disc florets which are bright yellow when immature fading to a soft yellow when mature.
3. Anemone flower form.
4. Ray florets are up to 25 mm long and 8 mm wide and flat.
5. Disc florets are up to 13 mm long and 3 mm wide and are funnelform.
6. Total flower diameter reaches 5.2 cm.
7. Compact, cushion growth habit.
8. Freely branching and profuse flowering.

9. Suitable for use as a garden mum for production in $4\frac{1}{2}$" to 1 gallon containers.

Jazz has not been observed under all possible environmental conditions. The phenotype may vary significantly with variations in environment such as temperature, light intensity, and day length. The following observations, measurements and comprisons describe plants grown in Parrish, Fla. under greenhouse conditions which approximate those generally used in commercial practice.

Of the many commercial cultivars known to the present inventors, the most similar in comparison to Jazz is Carmella. In comparison to Carmella, Jazz has a white flower with a yellow anemone center, is one week earlier in flower response, and has a more compact habit. The flower size and form of Jazz are similar to those same characteristics of Carmella.

The accompanying photographic drawing shows typical inflorescence and foliage characteristics of Jazz. Sheet 1 is a black and white photograph, with a few flowers hand painted to depict the true disc floret color of Jazz.

In the following description, color references are made to The Royal Horticultural Society Colour Chart. The color values were determined between 11:00 and 11:30 a.m. on Oct. 21, 1987 under fluorescent light at Parrish, Fla.

Classification:

*Botanical.*—*Chrysanthemum morifolium,* cv. Jazz.

*Commercial.*—Anemone garden mum.

INFLORESCENCE

A. Capitulum:

*Form.*—Flat.

*Type.*—Anemone.

*Diameter across face.*—Up to 5.2 cm.

B. Corolla of ray florets:

*Color (general tonality from a distance of three meters).*—White.

*Color (upper surface).*—155D.

*Color (under surface).*—155D.

C. Corolla of disc florets:

*Color (mature).*—5D.

*Color (immature).*—7A.

D. Reproductive organs:

*Androecium.*—Present in disc florets only.

*Gynoecium.*—Present in both disc and ray florets.

PLANT

A. General appearance:

*Height.*—20 cm when grown in the ground, given no long days and one pinch. Height will vary depending upon growing conditions.

B. Foliage:

*Color* (*upper surface*).—147A.

*Color* (*under surface*).—147B.

*Shape.*—Ovate, deeply lobed with serrate margins.

I claim:

1. A new and distinct cultivar of Chrysanthemum plant named Jazz, as illustrated and described, and parts thereof.

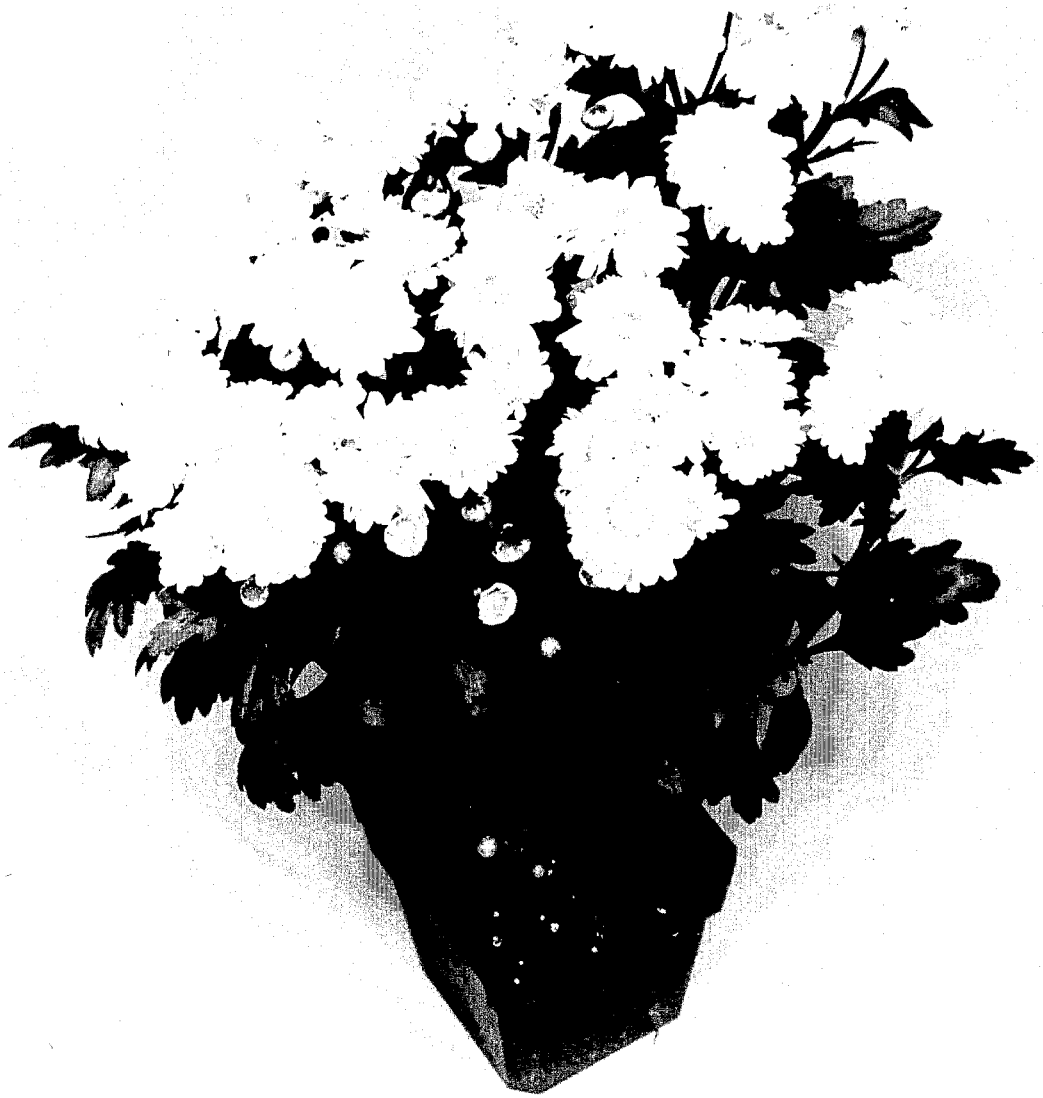

* * * * *